(12) United States Patent
Lim et al.

(10) Patent No.: US 7,843,323 B2
(45) Date of Patent: Nov. 30, 2010

(54) METHOD AND SYSTEM FOR RECOGNIZING DAILY ACTIVITIES USING SENSORS

(75) Inventors: Joon Ho Lim, Daejeon (KR); Hyun Chul Jang, Daejeon (KR); Jae Won Jang, Daejeon (KR); Sa Kwang Song, Daejeon (KR); Soo Jun Park, Seoul (KR); Seon Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 275 days.

(21) Appl. No.: 12/099,476

(22) Filed: Apr. 8, 2008

(65) Prior Publication Data

US 2009/0051524 A1    Feb. 26, 2009

(30) Foreign Application Priority Data

Aug. 20, 2007    (KR) .................... 10-2007-0083375

(51) Int. Cl.
*G08B 29/00*    (2006.01)
(52) U.S. Cl. ....................................................... 340/506
(58) Field of Classification Search ................. 340/506, 340/573.1, 539.13, 522, 604; 707/6
See application file for complete search history.

(56) References Cited

U.S. PATENT DOCUMENTS

| | | | |
|---|---|---|---|
| 6,825,769 B2 * | 11/2004 | Colmenarez et al. | 340/575 |
| 7,002,463 B2 * | 2/2006 | Wakabayashi | 340/522 |
| 7,009,497 B2 * | 3/2006 | Nicoletti et al. | 340/286.05 |
| 7,202,791 B2 | 4/2007 | Trajkovic | |
| 7,586,418 B2 * | 9/2009 | Cuddihy et al. | 340/573.1 |
| 7,619,366 B2 * | 11/2009 | Diederiks | 315/149 |
| 2005/0234310 A1 | 10/2005 | Alwan et al. | |

FOREIGN PATENT DOCUMENTS

| | | |
|---|---|---|
| JP | 2007-018525 A | 1/2007 |
| KR | 1020060122072 A | 11/2006 |

OTHER PUBLICATIONS

Matthai Philipose, et al; "Inferring Activities from Interactions with Objects", Pervasive Computing, IEEE, Oct.-Dec. 2004, vol. 3, Issue 4, pp. 50-57.

* cited by examiner

*Primary Examiner*—Phung Nguyen
(74) *Attorney, Agent, or Firm*—Ladas & Parry LLP

(57) ABSTRACT

There is provided a daily activity recognition system using sensors installed in required positions in a home to recognize daily activities of an old person, the system including: a radio frequency (RF) management unit receiving data measured by a plurality of sensors installed in required positions in a home, recognizing a corresponding sensor transmitting the received data, and converting the received data into a basic activity corresponding to the recognized sensor; a buffer management unit storing the basic activity received from the wireless processing manager in an internal buffer; and a daily activity recognition unit recognizing daily activities of an old person at each point in time previously set, based on the basic activity stored in the buffer. The daily activities of the old person are recognized and stored in a database, thereby providing various services related to the health of the old person.

18 Claims, 3 Drawing Sheets

METHOD AND SYSTEM FOR RECOGNIZING DAILY ACTIVITIES USING SENSORS

CROSS-REFERENCE TO RELATED APPLICATIONS

This application claims the priority of Korean Patent Application No. 10-2007-0083375 filed on Aug. 20, 2007, in the Korean Intellectual Property Office, the disclosure of which is incorporated herein by reference.

BACKGROUND OF THE INVENTION

1. Field of the Invention

The present invention relates to a daily activity recognition method and system, and more particularly, to a method and a system for recognizing daily activities of an old person by using sensors.

The present invention was supported by the IT R&D program of MIC/IITA [2006-S-007-02, titled: Ubiquitous Health Monitoring Module and System Development].

2. Description of the Related Art

In general, a method of recognizing daily activities, there are a vision-based method and radio frequency identification (RFID)-based method.

In the case of the vision-based method, a camera such as closed-circuit television (CCTV) is installed in a home and an activity is recognized by analyzing camera images. Via this method, daily activities of an old person may be recognized while the old person is not aware of that. However, in the vision-based method, since it is required to process moving pictures, complexity of processing is high, processing time is long, and it is difficult to provide high quality. Also, since it is required to install cameras in a home, a user may feel that the user is observed.

In the case of RFID-based method, an RFID tag is attached to things in a home and an old person wears a reader, thereby recognizing daily activities. The RFID-based method has an advantage that information on using things related to daily activities maybe directly known. However, since the old person should wear the reader that is big, it is difficult to apply the method to a real life. Also, when attaching an RFID tag to a material such as metal, a recognition function of the RFID tag is decreased.

SUMMARY OF THE INVENTION

An aspect of the present invention provides a daily activity recognition system in which sensors are installed on pieces of furniture and floors in a home to recognize daily activities and to directly know information on using goods related to the daily activities while an old person is unaware of this, the system capable of estimating a position and a posture of the old person by using the installed sensors and recognizing the daily activities based on a maintenance time of the estimated position and posture.

According to an aspect of the present invention, there is provided a daily activity recognition system using sensors, the system including: a radio frequency (RF) management unit receiving data measured by a plurality of sensors installed in required positions in a home, recognizing a corresponding sensor transmitting the received data, and converting the received data into a basic activity corresponding to the recognized sensor; a buffer management unit storing the basic activity received from the wireless processing manager in an internal buffer; and a daily activity recognition unit recognizing daily activities of an old person at each point in time previously set, based on the basic activity stored in the buffer.

According to another aspect of the present invention, there is provided a method of recognizing daily activities of an old person in a daily activity recognition system, the method including: receiving data measured by a plurality of sensors installed in required positions in a home in real time; recognizing a corresponding sensor transmitting the received data and converting the received data into a basic activity corresponding to the recognized sensor; storing the received basic activity received from an RF management unit, in an internal buffer; recognizing the daily activities of the old person based on the basic activity stored in the buffer for each present point in time; and storing the recognized daily activities in a database.

As described above, according to an exemplary embodiment of the present invention, daily activities of an old person are recognized by installing sensors in required positions in a home and the recognized daily activities are accumulated in a database, thereby providing various services related to the health of the old person.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Exemplary embodiments of the present invention will now be described in detail with reference to the accompanying drawings. Only, in describing operations of the exemplary embodiments in detail, when it is considered that a detailed description on related well-known functions or constitutions may make essential points of the present invention be unclear, the detailed description will be omitted.

In an exemplary embodiment of the present invention, a sensor measuring a pressure of an object put on the sensor is installed on pieces of furniture and floors in a home. Hereinafter, the present embodiment will be described employing a pressure sensor. However, various sensors such as a thermal sensor capable of recognizing daily activities of an old person may be used.

Figure 1:
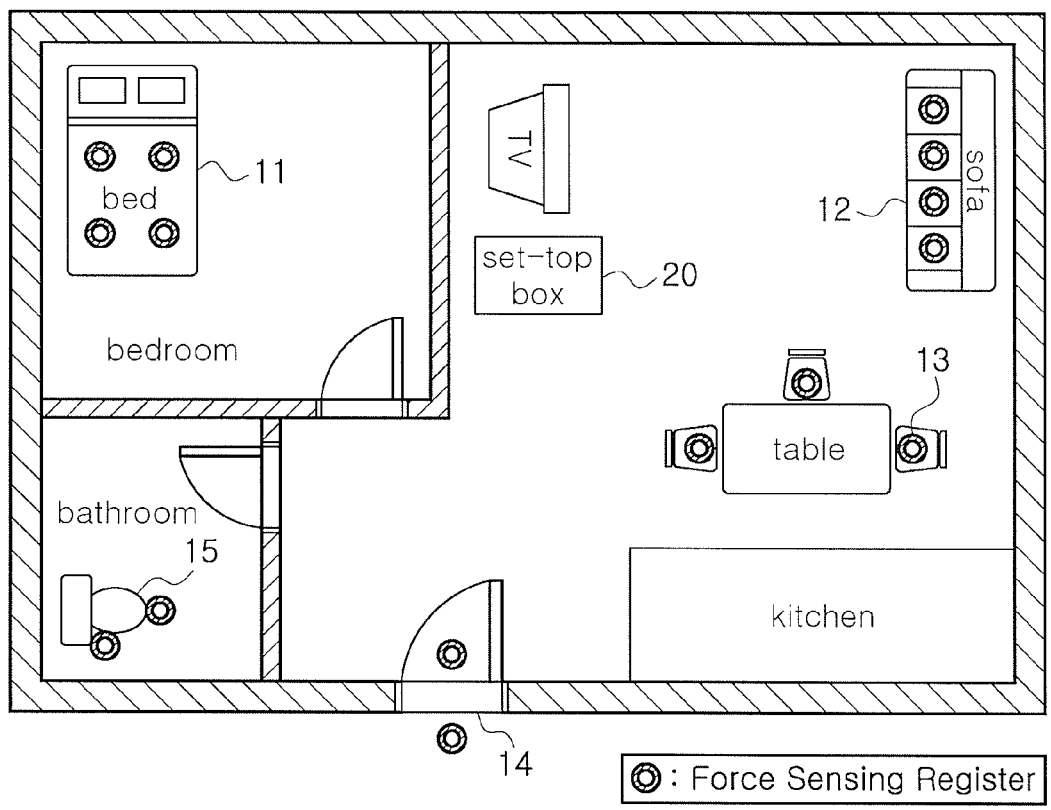
FIG. 1 is a diagram illustrating sensors installed in required positions in a home, according to an exemplary embodiment of the present invention.

An example of installing pressure sensors (hereinafter, referred to as sensors) is shown in FIG. 1. The example of installing sensors will be described with reference to FIG. 1.

To recognize daily activities of an old person in a home, sensors are installed pieces of furniture and floors of a place where the old person generally lives. For example, the sensors may be installed on a bed 11 to recognized a sleep, on a sofa 12 to recognize a rest, on a table and table chairs 13 to recognize a meal, on a front of a toilet bowl and a lever for the toilet bowl 14 to recognize an excretion, bottoms 15 of both sides of a door to recognize a go-out. For example, four or more of sensors are installed on top areas of the bed 11, the sofa 12, and table and table chairs 13 and one or more of sensors are installed on the front of the toilet bowl and the lever for the toilet bowl 14 and the bottoms 15 of the both sides of the door. Also, when necessary, the sensors may be installed certain positions indoor or outdoor.

The sensors may include a measuring unit measuring a pressure and a transmitting unit transmitting a measured value.

The measuring unit is a polymer thick film device having characteristics in which resistance decrease when a vertical force increases a surface of a polymer thick film, which measures a pressure of an object put on the sensor via a resistance value.

The transmitting unit is a radio frequency (RF) communication device, which transmits the resistance value to a set-top box 20 installed in a home.

The sensors communicate via the same channel with a bandwidth of 2.4 GHz, are distinguished by particular identification for each sensor, and transmit 32-bit data as shown in Table 1.

TABLE 1

| Number of bits | Value | Range of expression |
|---|---|---|
| 0-3 | Sensor type | 0-15 |
| 4-13 | Sensor identification | 0-1023 |
| 14-15 | Sensor state | 00, 01, 10, 11 |
| 16-31 | Sensor value | 0-1023 |

The sensor type is a field considering an additional sensor. The sensors have the same value.

The sensor identification has a particular value previously defined for each sensor installed in the home.

The sensor state shows a state change of ON and OFF based on the sensor value. In this case, a certain threshold value is determined according to a piece of furniture where the sensor is installed and it is determined as ON when less than the threshold value and is determined as OFF when more than the threshold value. In the case of the sensor state, 00 indicates OFF->OFF, 01 indicates OFF->ON, 10 indicates ON->OFF, and 11 indicates ON CONTINUE. Accordingly, data transmission is performed for each 0.5 second at a point in time when the sensor state is changed and ON CONTINUE.

The sensor value shows a degree of a resistance value measured at a force sensing resistor (FSR) sensor. The greater pressure value, the lower resistance value.

A method and a system for recognizing daily activities of an old person by using data measured at sensors installed in required positions in a home, as shown in FIG. 1, will be described.

A configuration of the system for recognizing daily activities will be described in detail with reference to FIG. 2.

Figure 2:
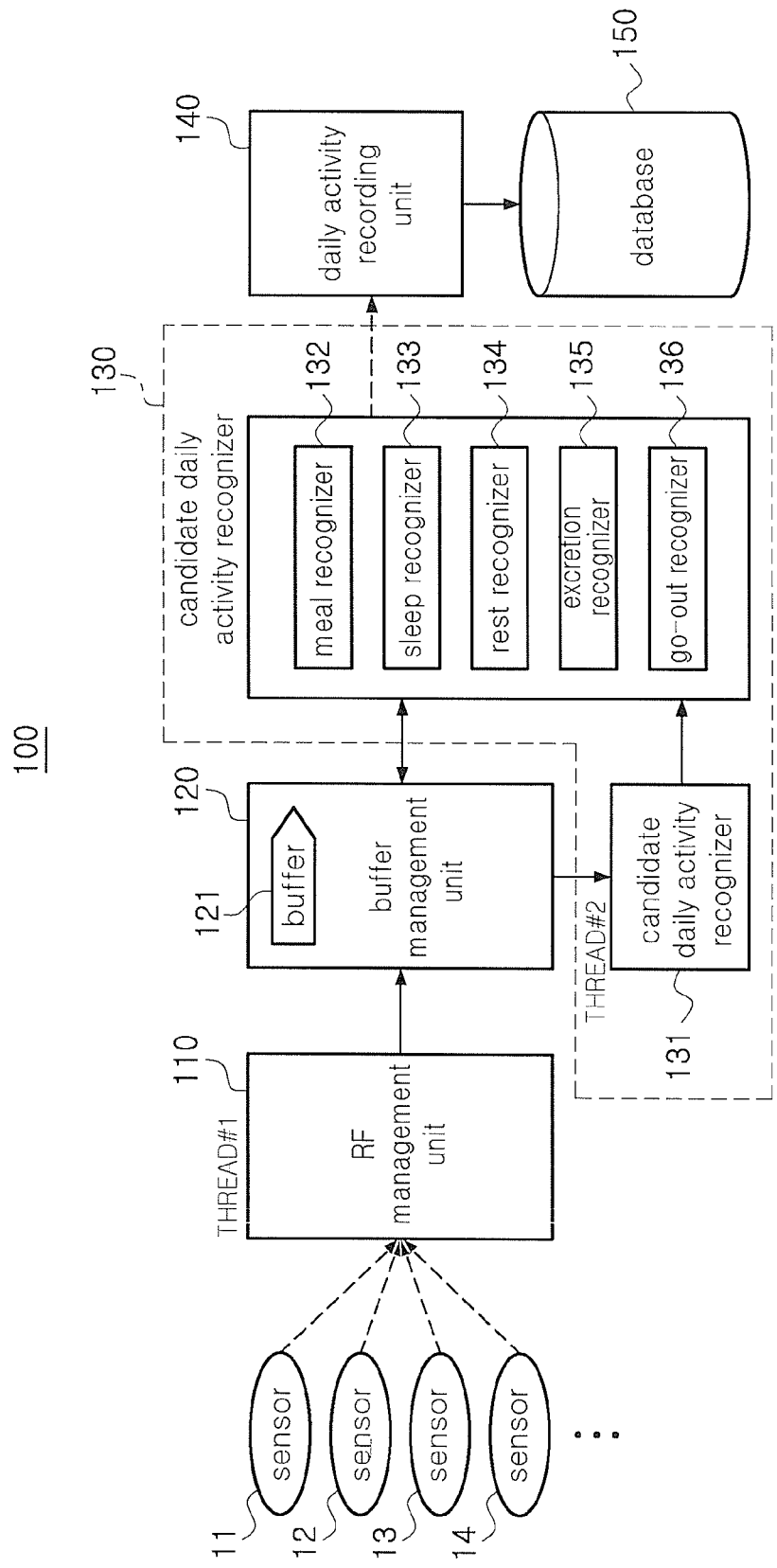
FIG. 2 is a diagram illustrating a configuration of a daily activity recognition system according to an exemplary embodiment of the present invention.

FIG. 2 is a diagram illustrating the system according to an exemplary embodiment of the present invention.

Referring to FIG. 2, the system 100 may include a radio frequency (RF) management unit 110, a buffer management unit 120, a daily activity recognition unit 130, an activity recoding unit 140, and a database 150.

The RF management unit 110 receives data measured in real time from the sensors 11 to 15, recognizes a sensor transmitting the received data based on sensor identification, and converts the received data into a basic activity, which is one of a table-based activity (TABLE), abed-based activity (BED), a sofa-based activity (SOFA), a first toilet-based activity (TOILET), a second lever-based activity (LEVER), a first go-out-based activity (GO-OUT), and a come-in-based activity (COME-IN). The basic activity may include other activities in addition to the described above. In this case, the table-based activity indicates a basic activity when one or more of sensors installed on a table chair are turned ON. The bed-based activity indicates a basic activity when two or more of sensors installed on a bed are turned ON. The sofa-based activity indicates a basic activity when two or more of sensors installed on a sofa. The toilet-based activity indicates a basic activity when a sensor installed on a front bottom of a toilet bowl is turned ON. The lever-based activity indicates a basic activity when a sensor installed on a lever for the toilet bowl is turned ON. The go-out-based activity indicates a basic activity when sensors installed on a bottom of a door are sequentially turned ON from inside to outside. The come-in-based activity indicates a basic activity when the sensors installed on the bottom of the door are sequentially turned ON from outside to inside. Also, the RF management unit 110 compares the converted basic activity with a previous basic activity and stores the converted basic activity together with present time information in the buffer management unit 120 when the converted basic activity is different from the previous basic activity.

The buffer management unit 120 includes a buffer 121, checks the present time information inputted from the RF management unit 110, and stores the converted basic activity in the buffer 121 in the order of time. The buffer management unit 120 deletes basic activities recognized as daily activities via each recognitions for daily activities.

The daily activity recognition unit 130 includes a candidate daily activity recognizer 131, a meal recognizer 132, a sleep recognizer 133, a rest recognizer 134, an excretion recognizer 135, and a go-out recognizer 136, which are daily activity recognizer, and a timer (not shown). The daily activity recognition unit 130 checks contents of the buffer management unit 120, that is, contents of stored basic activities for a certain time preset in the timer, extracts candidate daily activities according to the checked contents, and transmits the extracted candidate daily activities to a corresponding daily activity recognizer. In this case, a basic activity corresponding to each daily activity is shown in Table 2.

TABLE 2

| Daily activities | Basic activities |
|---|---|
| Meal activity | Table-based activity |
| Sleep activity | Bed-based activity |
| Rest activity | Sofa-based activity |
| Excretion activity | Toilet and lever-based activities |
| Go-out activity | Go-out and come-in-based activities |

The meal recognizer 132 recognizes a meal activity based on a table-based activity. In this case, the table-based activity is a basic activity when a person sits on a table chair and foods are put on the table. Accordingly, the meal recognizer 132 does not recognize as a meal when an old person sit on the table chair without taking a meal. As a reference for recognizing a meal, there are a reference time and an ordinary meal-maintenance time. That is, a probability value increases as the meal time is close to an reference meal time or the maintenance time is similar to an ordinary meal maintenance time. The meal recognizer 132 estimates a reference time and a ordinary maintenance time for each user, based on data accumulated in the database 150. When the probability value based on the reference time and the maintenance time is greater than a certain value, the meal recognizer 132 recognizes as the meal. In this case, the reference time is shown as a Gaussian mixture of normal distribution estimated for each of a breakfast, a lunch, and a dinner. The maintenance time is shown as normal distribution.

The sleep recognizer 133 recognizes a sleep activity based on a bed-based activity. In this case, the bed-based activity is an activity when two or more sensors are turned ON. Accordingly, excluding a case in which the old person sits on a bed, only a case in which the persona lies on the bed may be recognized as the sleep activity. The sleep recognizer 133 recognizes the sleep activity based on a reference sleep time and a sleep maintenance time, similar to the meal activity. The reference time and the maintenance time are estimated as normal distribution based on the data accumulated in the database 150. Accordingly, the sleep recognizer 133 recognizes as the sleep activity when a probability value is greater than a certain value based on the reference time and the maintenance time.

The rest recognizer 134 recognizes a rest activity based on a maintenance time of a sofa-based activity. In this case, a rest in the daily activities indicates watching TV or reading on a sofa for a long time, excluding an activity of sitting on the sofa for a short while. In this case, the maintenance time of the sofa-based activity includes activities of standing and walking for a short while or going to a bathroom. For this, the rest recognizer 134 calculates the maintenance time including a break for a short time within the sofa-based activity. To calculate the maintenance time, the rest recognizer 134 recognizes the rest activity based on an existing maintenance time of the sofa-based activity when the sofa-based activity does not occur for a certain amount of time. For example, when the maintenance time of the rest activity is greater than 30 minutes, from a start point in time to an end point in time of the maintenance is recognized as the rest activity.

The excretion recognizer 135 recognizes an excretion activity based on a toilet and lever-based activities. The excretion activity is not divided into feces or urine. The excretion recognizer 135 recognizes as the excretion activity from a point in time when the toilet-based activity occurs to a point in time when the lever-based activity starts since the basic activities guarantees the daily activity. Also, when the toilet-based activity occurs but the lever-based activity does not occur, it is considered as the old person tries to relieve nature but does not succeed due to weakening of an urinary function, which is not recognized as the excretion activity.

The go-out recognizer 136 recognizes a go-out activity based on a time interval between a go-out-based activity and a come-in-based activity. When the time interval is more than a certain amount of time, for example, 30 minutes, the go-out recognizer 136 recognizes an amount of time from a point in time of going-out to a point in time of coming-in, as the go-out activity. When the time interval is short, the go-out recognizer 136 considers as daily activities associated with a door, such as throwing trashes out and does not recognize as the go-out activity.

the database 150 stores daily activities recognized at the daily activity recognition unit 130. An example of the recognized daily activities stored in the database 150 is as shown in Table 3.

TABLE 3

| Start time | End time | Daily activity |
| --- | --- | --- |
| 2007-07-01 09:05:02 | 2007-07-01 11:50:28 | Go-out activity |
| 2007-07-01 12:10:37 | 2007-07-01 12:38:13 | Meal activity |

The method of recognizing the daily activities of the old person in the system 100 will be described in detail.

When receiving real-time measured data from the sensors, the RF management unit 110 checks a sensor transmitting the measured data by using sensor identification thereof and converts the data into a basic activity according to a position where the sensor is installed. The RF management unit 110 stores and manages the converted basic activity in the order of time in the buffer management unit 120.

In this case, the daily activity recognition unit 130 recognizes the daily activities of the old person, based on the basic activity stored in the buffer management unit 120.

Figure 3:
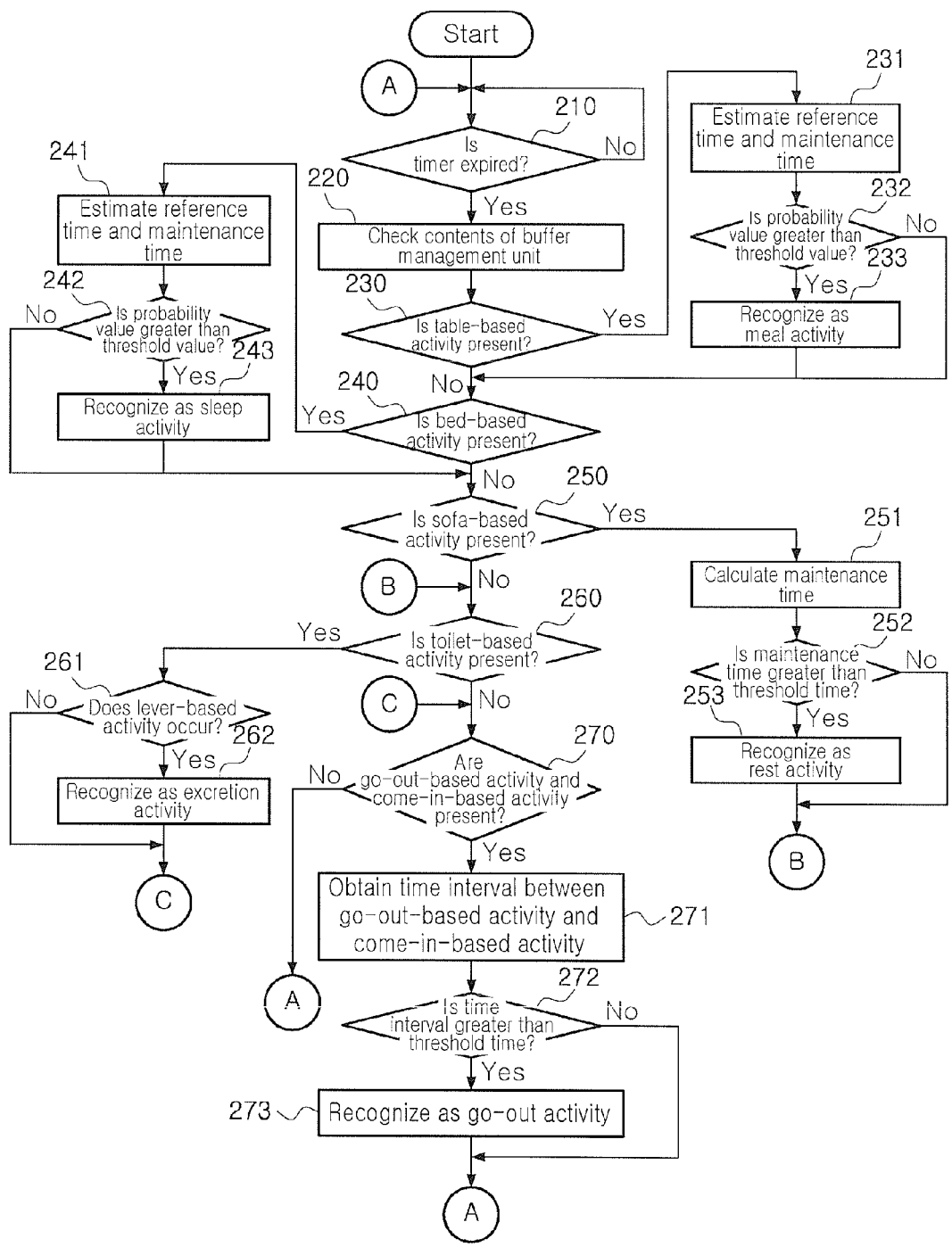
FIG. 3 is a flowchart illustrating a process of recognizing daily activities at a daily activity recognition unit according to an exemplary embodiment of the present invention.

FIG. 3 is a flowchart illustrating a process of recognizing daily activities at the daily activity recognition unit 130, according to an exemplary embodiment of the present invention.

Referring to FIG. 3, in 210, the daily activity recognition unit 130 checks whether a timer included in the candidate daily activity recognizer 131 is expired and continuously waits when the timer is not expired. On the other hand, when the timer is expired, the daily activity recognition unit 130 checks contents stored in the buffer management unit 120 and extracts candidate daily activities in 220.

The daily activity recognition unit 130 checks each basic activity corresponding to each of the candidate daily activities extracted and recognizes the each basic activity as a corresponding daily activity such as a meal activity, a sleep activity, a rest activity, an excretion activity, and a go-out activity.

In 230, the daily activity recognition unit 130 checks the extracted candidate daily activity. When there is present a table-based activity, in 231, a reference meal time and a meal maintenance time are estimated and a probability value is obtained based thereon. In 232, the daily activity recognition unit 130 checks whether the obtained probability value is greater than a threshold value. As a result of the checking, when the probability value is greater than the threshold value, in 233, the daily activity recognition unit 130 recognizes the extracted candidate daily activity as the meal activity. After the meal activity is recognized or when the probability value is smaller than the threshold value, the daily activity recognition unit 130 performs 240.

As a result of the checking in 230, when the table-based activity is not present, in 240, the daily activity recognition unit 130 checks whether a bed-based activity is present. As a result of the checking, when there is present the bed-based activity, in 241, the daily activity recognition unit 130 estimates a reference sleep time and a sleep maintenance time and a probability value is obtained based thereon. In 242, it is checked whether the obtained probability value is greater than a threshold value. As a result of the checking, when the probability value is greater than the threshold value, in 243, the daily activity recognition unit 130 recognizes the extracted candidate daily activity as the sleep activity. After the sleep activity is recognized or when the probability value is smaller than the threshold value, the daily activity recognition unit 130 performs 250.

As a result of the checking in 240, when there is not present the bed-based activity, in 250, the daily activity recognition unit 130 checks whether there is present a sofa-based activity. As a result of the checking, when there is present the sofa-based activity, in 251, the daily activity recognition unit 130 calculates a maintenance time of a rest, including a break within the sofa-based activity. In 252, the daily activity recognition unit 130 checks whether the calculated maintenance time is greater than a preset threshold time. As a result of the checking, when the maintenance time is greater than the threshold time, in 253, an activity performed in an amount of time from a point in time when the maintenance time starts to a point in time when the maintenance time ends is recognized as the rest activity. After the rest activity is recognized or when the maintenance is smaller than the threshold time, the daily activity recognition unit 130 performs 260.

As a result of the checking in 250, when there is not present the sofa-based activity, in 260, the daily activity recognition unit 130 checks whether there is present a toilet-based activity. As a result of the checking, when there is present the toilet-based activity, in 261, the daily activity recognition unit 130 checks whether there is present a lever-based activity. As a result of the checking, when the lever-based activity occurs, in 262, the daily activity recognition unit 130 recognizes an activity performed in an amount of time from a point in time when the toilet-based activity starts to a point in time when the lever-based activity starts, as the excretion activity. After the excretion activity is recognized or when the lever-based activity does not occur, the daily activity recognition unit 130 performs 270.

As a result of the checking in 260, when there is not present the toilet-based activity, in 270, the daily activity recognition unit 130 checks whether there are present a go-out-based activity and a come-in-based activity. As a result of the checking, when there are present the go-out-based activity and the come-in-based activity, in 271, the daily activity recognition unit 130 obtains a time interval between the go-out-based activity and the come-in-based activity. In 272, the daily activity recognition unit 130 checks whether the obtained time interval is greater than a preset threshold time. When the time interval is greater than the threshold time, in 273, the daily activity recognition unit 130 recognizes an activity performed in an amount of time from a point in time when the go-out-based activity starts to a point of time when the come-in-based activity starts, as the go-out activity. After this, the daily activity recognition unit 130 returns to 210 and repeatedly performs the process as described above for a certain time.

As described above, daily activities recognized at the daily activity recognition unit 130 are transferred to the daily activity recording unit 140. In this case, basic activities recognized as daily activities via daily activity recognition are deleted from the buffer management unit 120.

The daily activity recording unit 140 records the received daily activity in the database 150.

As described above, the system 100 for recognizing daily activities may receive measured data from sensors installed in required positions in a home, estimate activities that an old person performs at a certain place and a maintenance time thereof, and recognize daily activities of the old person.

Also, the system 100 may be applied to sense symptoms such as a change of excretion numbers of the old person and changes of meal and sleep patterns of the old person, based on activity data accumulated in a database.

Accordingly, in the present embodiment, when an old person lives alone, family living in a distant place may check daily activities of the old person via web. For example, when the old person suffers from senile dementia or diabetes, frequencies of meals and excretions may be known.

While the present invention has been shown and described in connection with the exemplary embodiments, it will be apparent to those skilled in the art that modifications and variations can be made without departing from the spirit and scope of the invention as defined by the appended claims.

What is claimed is:

1. A daily activity recognition system using sensors, the system comprising:
    a radio frequency (RF) management unit receiving data measured by a plurality of sensors installed in required positions in a home, recognizing a corresponding sensor transmitting the received data, and converting the received data into a basic activity corresponding to the recognized sensor;
    a buffer management unit storing the basic activity received from the wireless processing manager in an internal buffer; and
    a daily activity recognition unit recognizing daily activities of an old person at each point in time previously set, based on the basic activity stored in the buffer,
    wherein the daily activity recognition unit comprises:
    a candidate daily activity recognizer checking contents of the basic activities stored in the buffer management unit for each point in time previously set and extracting candidate daily activities by using the checked contents; and
    a plurality of daily activity recognizers recognizing the daily activities of the old person, corresponding to the basic activities included in the extracted candidate daily activities.

2. The system of claim 1, further comprising a daily activity recording unit receiving the daily activities recognized by the daily activity recognizer and recoding the received daily activity in a database.

3. The system of claim 1, wherein the RF management unit compares the converted basic activity with a previous basic activity and transmits the converted basic activity together with a present time when the converted basic activity is different from the previous basic activity.

4. The system of claim 3, wherein the converted basic activity comprises one or more of a table-based activity, a bed-based activity, a sofa-based activity, and a first toilet-based activity, a second lever-based activity, a first go-out-based activity, and a second come-in-based activity.

5. The system of claim 1, wherein the plurality of daily activity recognizers comprise:
    a meal recognizer recognizing a meal activity based on the table-based activity when the table-based activity is present in the extracted candidate daily activities;
    a sleep recognizer recognizing a sleep activity based on the bed-based activity when the bed-based activity is present in the extracted candidate daily activities;
    a rest recognizer recognizing a rest activity based on the sofa-based activity when the sofa-based activity is present in the extracted candidate daily activities;
    an excretion recognizer recognizing an excretion activity based on the first toilet-based activity and the second lever-based activity when the first toilet-based activity and the second lever-based activity are present in the extracted candidate daily activities; and
    a go-out recognizer recognizing a go-out activity based on the first go-out-based activity and the second come-in-based activity when the first go-out-based activity and the second come-in-based activity are present in the extracted candidate daily activities.

6. The system of claim 5, wherein the meal recognizer estimates a probability value based on a reference meal time and a meal-maintenance time and recognizes as the meal activity when the estimated probability value is greater than a preset threshold value.

7. The system of claim 5, wherein the sleep recognizer estimates a probability value based on a reference sleep time and a sleep-maintenance time and recognizes as the sleep activity when the estimated probability value is greater than a preset threshold value.

8. The system of claim 5, wherein the rest recognizer calculates a maintenance time comprising a break for a short time within the sofa-based activity and recognizes a start point in time and an end point in time as the rest activity when the calculated maintenance time is greater than a preset threshold time.

9. The system of claim 5, wherein the excretion recognizer recognizes an amount of time from a point in time when the first toilet-based activity occurs to a point in time when the second lever-based activity starts, as the excretion activity.

10. The system of claim 9, wherein the excretion recognizer does not recognizes as the excretion activity when the first toilet-based activity occurs and the second lever-based activity does not occur.

11. The system of claim 5, wherein the go-out recognizer, when a time interval between the first go-out-based activity and the second come-in-based activity is greater than a preset threshold time, recognizes an amount of time from a point in time when the first go-out activity to a point in time when the second come-in activity starts, as the go-out activity.

12. A method of recognizing daily activities of an old person in a daily activity recognition system, the method comprising:
receiving data measured by a plurality of sensors installed in required positions in a home in real time;
recognizing a corresponding sensor transmitting the received data and converting the received data into a basic activity corresponding to the recognized sensor;
storing the received basic activity received from a radio frequency (RF) management unit, in an internal buffer;
recognizing the daily activities of the old person based on the basic activity stored in the buffer for each present point in time; and
storing the recognized daily activities in a database.
wherein the recognizing the daily activities of the old person for each preset point in time comprises:
checking contents of the basic activity stored in the buffer, for the each preset point in time;
extracting candidate daily activities by using the checked contents; and
recognizing each of the daily activities of the old person, corresponding to a basic activity included in the extracted candidate daily activities.

13. The method of claim 12, wherein the recognizing each of the daily activities of the old person comprises:
recognizing a meal activity based on a table-based activity when the table-based activity is present in the extracted candidate daily activities;
recognizing a sleep activity based on a bed-based activity when the bed-based activity is present in the extracted candidate daily activities;
recognizing a rest activity based on a sofa-based activity when the sofa-based activity is present in the extracted candidate daily activities;
recognizing an excretion activity based on a first toilet-based activity and a second lever-based activity when the first toilet-based activity and the second lever-based activity are present in the extracted candidate daily activities; and
recognizing a go-out activity based on a first go-out-based activity and a second come-in-based activity when the first go-out-based activity and the second come-in-based activity are present in the extracted candidate daily activities.

14. The method of claim 13, wherein the recognizing a meal activity comprises:
estimating a probability value based on a reference time and a maintenance time with respect to a meal;
comparing the estimated probability value with a preset threshold value; and
recognizing as the meal activity when the estimated probability value is greater than the threshold value.

15. The method of claim 13, wherein the recognizing a sleep activity comprises:
estimating a probability value based on a reference time and a maintenance time with respect to a sleep;
comparing the estimated probability value with a preset threshold value; and
recognizing as the sleep activity when the probability value is greater than the threshold value.

16. The method of claim 13, wherein the recognizing a rest activity comprises:
calculating a maintenance time including a break for a short time within the sofa-based activity;
comparing the calculated maintenance time with a preset threshold time; and
recognizing an amount of time from a point in time when the maintenance time starts and a point in time when the maintenance time is finished, when the maintenance time is greater than the threshold time.

17. The method of claim 13, wherein the recognizing an excretion activity comprises:
checking whether the second lever-based activity occurs;
recognizing an amount of time from a point in time when the first toilet-based activity starts to a point in time when the second lever-based activity starts, when the second lever-based activity occurs; and
recognizing as the excretion activity does not occur, when the second lever-based activity does not occur.

18. The method of claim 13, wherein the recognizing a go-out activity comprises:
obtaining a time interval between the first go-out-based activity and the second come-in-based activity;
comparing the obtained time interval with a preset threshold time; and
recognizing an amount of time from a point in time when the first go-out-based activity starts to a point in time when the second come-in-based activity starts, as the go-out activity, when the time interval is greater than the threshold time.

* * * * *